United States Patent [19]

Nishina et al.

[11] Patent Number: 5,770,432
[45] Date of Patent: Jun. 23, 1998

[54] OBESITY ASSOCIATED GENES

[75] Inventors: Patsy Nishina; Konrad Noben-Trauth; Juergen Naggert, all of Bar Harbor, Me.; Michael North, La Jolla, Calif.

[73] Assignees: Sequana Therapeutics, La Jolla, Calif.; Jackson Laboratory, Bar Harbor, Me.

[21] Appl. No.: 630,592

[22] Filed: Apr. 10, 1996

[51] Int. Cl.$^6$ .............................. C07H 21/04; C12Q 1/68; C12N 15/74; C12N 15/85

[52] U.S. Cl. .......................... 435/252.3; 435/6; 435/325; 536/23.1; 536/24.31; 536/23.5

[58] Field of Search ...................... 435/6, 240.2, 252.3, 435/325, 69.1, 172.3; 536/23.5, 24.31, 23.1

[56] References Cited

U.S. PATENT DOCUMENTS 5,646,040  7/1997  Kleyn et al. ............................ 435/325

OTHER PUBLICATIONS

Lee et al., "Abnormal Splicing of the Leptin Receptor in Diabetic Mice," Nature (Feb. 1996), 379:632–635.
Ohlemiller et al., "Cochlear and Retinal Degeneration in the Tubby Mouse," NeuroReport (Apr. 1995), 6:845–849.
Samuelson et al., "Localization of the Murine Cholecystokinin A and B Receptor Genes," Mammalian Genome (1995), 6:242–246.
Zhang et al., "Positional Cloning of the Mouse Obese Gene and its Human Homologue," Nature (Dec. 1994), 372:425–432.
Nishina et al., "Characterization of Plasma Lipids in Genetically Obese Mice: The Mutants Obese, Diabetes, Fat, Tubby, and Lethal Yellow," Metabolism (May 1994), 43:549–553.
Jones et al., "Localization of Insulin–2 (Ins–2) and the Obesity Mutant Tubby (tub) to Distinct Regions of Mouse Chromosome 7," Genomics (1992), 14:197–199.
Coleman and Eicher, "Fat (fat) and Tubby (tub): Two Autosomal Recessive Mutations Causing Obesity Syndromes in the Mouse," J. of Heredity (1990), 81:424–427.

*Primary Examiner*—Jasemine C. Chambers
*Assistant Examiner*—Scott D. Priebe
*Attorney, Agent, or Firm*—Pamela J. Sherwood; Bozicevic & Reed LLP

[57] ABSTRACT

The gene responsible for the autosomal recessive mouse obesity mutation tub was identified by positional cloning. The homologous human gene is also provided. The genes are used to produce tubby protein; in screening for compositions that modulate the expression or function of the tubby protein; and in studying associated physiological pathways. The DNA is further used as a diagnostic for genetic predisposition to obesity, retinal degeneration or cochlear degeneration. The mutation responsible for the tub phenotype is a G to T transversion that abolishes a donor splice site in the 3' coding region and results in a larger transcript containing the unspliced intron. A second, prematurely truncated transcript arises from the introduction of a premature polyadenylation site in the unspliced intron.

6 Claims, 1 Drawing Sheet

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 2119 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

```
ATCAGCCCAA GATGGAGGCA GGCTAGTTTA TCACTACCTG TATCTTATCT GCTAGCCAAT      60

GGTACTAAAA CCTATGGCTC AGTGTCCCTC TTCCCAACCA GGAAATGTGG AAGACAGTGG     120

GAAAGGAAGG ACCGTGCTCG TGGAAAACAG CCTCTGACCC CAGACACAAC TGTATGGAAA     180

GTCCAGGGCT GTGTGACAGT TCCTGTGACA GGAAAACACC TCCCCGTGTG GCACCAGGCA     240

GTGAGATGTC CCTAGACATT TTCATTGGCA CCGAGGAAGG CATGTTCTTT GGTATGCTTA     300

GCCGAGACCA ACACCTGGAA TGATACCAGG TGGCTGCCTC TGACCCCAAC ACTGTGCTTG     360

GAAAGAATGT AGCCTGTGAC TTCTAGTAAA AGTGTCCTAG ATGATGAGGG CAGCAACCTG     420

AGGCAGCAGA AGCTCGACCG GCAGCGGGCC CTGTTGGAAC AGAAGCAGAA GAAGAAGCGC     480

CAAGAGCCCT TGATGGTACA GGCCAATGCA GATGGACGGC CCCGGAGTCG GCGAGCCCGG     540

CAGTCAGAGG AGCAAGCCCC CCTGGTGGAG TCCTACCTCA GCAGCAGTGG CAGCACCAGC     600
```

```
TACCAAGTTC  AAGAGGCCGA  CTCGATTGCC  AGTGTACAGC  TGGGAGCCAC  CCGCCCACCA    660

GCACCAGCCT  CAGCCAAGAA  ATCCAAGGGA  GCGGCTGCAT  CTGGGGGCCA  GGGTGGAGCC    720

CCTAGGAAGG  AGAAGAAGGG  AAAGCATAAA  GGCACCAGCG  GGCCAGCAAC  TCTGGCAGAA    780

GACAAGTCTG  AGGCCCAAGG  CCCAGTGCAG  ATCTTGACTG  TGGGACAGTC  AGACCACGAC    840

AAGGATGCGG  GAGAGACAGC  AGCCGGCGGG  GGCGCACAGC  CCAGTGGGCA  GGACCTCCGT    900

GCCACGATGC  AGAGGAAGGG  CATCTCCAGC  AGCATGAGCT  TTGACGAGGA  CGAGGATGAG    960

GATGAAAACA  GCTCCAGCTC  CTCCCAGCTA  AACAGCAACA  CCCGCCCTAG  TTCTGCCACT   1020

AGCAGAAAGT  CCATCCGGGA  GGCAGCTTCA  GCCCCAGCC  CAGCCGCCCC  AGAGCCACCA   1080

GTGGATATTG  AGGTCCAGGA  TCTAGAGGAG  TTTGCACTGA  GGCCAGCCCC  ACAAGGGATC   1140

ACCATCAAAT  GCCGCATCAC  TCGGGACAAG  AAGGGGATGG  ACCGCGGCAT  GTACCCCACC   1200

TACTTTCTGC  ACCTAGACCG  TGAGGATGGC  AAGAAGGTGT  TCCTCCTGGC  GGGCAGGAAG   1260

AGAAAGAAGA  GTAAAACTTC  CAATTACCTC  ATCTCTGTGG  ACCCAACAGA  CTTGTCTCGG   1320

GGAGGCGATA  GCTATATCGG  GAAGTTGCGG  TCCAACCTGA  TGGGCACCAA  GTTCACCGTT   1380

TATGACAATG  GCGTCAACCC  TCAGAAGGCA  TCCTCTTCCA  CGCTGGAAAG  CGGAACCTTG   1440

CGCCAGGAGC  TGGCAGCGGT  GTGCTATGAG  ACAAATGTCC  TAGGCTTCAA  GGGACCTCGG   1500

AAGATGAGTG  TGATCGTCCC  AGGCATGAAC  ATGGTTCATG  AGAGAGTCTG  TATCCGCCCC   1560

CGCAATGAAC  ATGAGACCCT  GTTAGCACGC  TGGCAGAACA  AGAACACGGA  GAGCATCATT   1620

GAGCTGCAGA  ACAAGACGCC  AGTCTGGAAT  GATGACACAC  AGTCCTATGT  ACTTAACTTC   1680

CACGGCCGTG  TCACACAGGC  TTCTGTGAAG  AACTTCCAGA  TCATCCACGG  CAATGACCCG   1740

GACTACATCG  TCATGCAGTT  TGGCCGGGTA  GCAGAAGATG  TGTTCACCAT  GGATTACAAC   1800

TACCCACTGT  GTGCACTGCA  GGCCTTTGCC  ATTGCTCTGT  CCAGCTTTGA  CAGCAAGCTG   1860

GCCTGCGAGT  AGAGGCCCCC  ACTGCCTTTA  GGTGGCCCAG  TCCGGAGTGG  AGCTTGCCTG   1920

CCTGCCAAGA  CAGCCCTGCC  TACCCTCTGT  TCATAGGCCC  TCTATGGGCT  TTCTGGCCTT   1980

ACCAACCAGA  GACTGGCTGC  TCTGCCTCTG  CTGCTGAAGC  AGGGGGGACA  GCAAATGGGT   2040

ATGACAGGAG  AAGAATATTT  CTGTGCCCCA  AGGTCAACAA  CACACATGCC  CAGTCCTGGA   2100

AAAAAAAAAA  AAAAAAAA                                                    2119
```

( 2 ) INFORMATION FOR SEQ ID NO:2:

( i ) SEQUENCE CHARACTERISTICS:
        ( A ) LENGTH: 459 amino acids
        ( B ) TYPE: amino acid
        ( C ) STRANDEDNESS: double
        ( D ) TOPOLOGY: linear ( i i ) MOLECULE TYPE: peptide ( x i ) SEQUENCE DESCRIPTION: SEQ ID NO:2:

```
Met  Val  Gln  Ala  Asn  Ala  Asp  Gly  Arg  Pro  Arg  Ser  Arg  Arg  Ala  Arg
 1              5                   10                  15

Gln  Ser  Glu  Glu  Gln  Ala  Pro  Leu  Val  Glu  Ser  Tyr  Leu  Ser  Ser
         20                  25                  30

Gly  Ser  Thr  Ser  Tyr  Gln  Val  Gln  Glu  Ala  Asp  Ser  Ile  Ala  Ser  Val
              35                  40                  45

Gln  Leu  Gly  Ala  Thr  Arg  Pro  Pro  Ala  Pro  Ala  Ser  Ala  Lys  Lys  Ser
         50                  55                  60

Lys  Gly  Ala  Ala  Ala  Ser  Gly  Gly  Gln  Gly  Gly  Ala  Pro  Arg  Lys  Glu
 65                  70                  75                  80
```

| | | | | | | | | | | | | | |
|---|---|---|---|---|---|---|---|---|---|---|---|---|---|
|Lys|Lys|Gly|Lys|His 85|Lys|Gly|Thr|Ser|Gly 90|Pro|Ala|Thr|Leu|Ala 95|Glu
|Asp|Lys|Ser|Glu 100|Ala|Gln|Gly|Pro|Val 105|Gln|Ile|Leu|Thr|Val 110|Gly|Gln
|Ser|Asp|His 115|Asp|Lys|Asp|Ala|Gly 120|Glu|Thr|Ala|Ala|Gly 125|Gly|Gly|Ala
|Gln|Pro 130|Ser|Gly|Gln|Asp|Leu 135|Arg|Ala|Thr|Met|Gln 140|Arg|Lys|Gly|Ile
|Ser 145|Ser|Ser|Met|Ser|Phe 150|Asp|Glu|Asp|Glu 155|Asp|Glu|Asp|Glu|Asn|Ser 160
|Ser|Ser|Ser|Ser|Gln 165|Leu|Asn|Ser|Asn|Thr 170|Arg|Pro|Ser|Ser|Ala 175|Thr
|Ser|Arg|Lys|Ser 180|Ile|Arg|Glu|Ala|Ala 185|Ser|Ala|Pro|Ser|Pro 190|Ala|Ala
|Pro|Glu|Pro 195|Pro|Val|Asp|Ile|Glu 200|Val|Gln|Asp|Leu|Glu 205|Glu|Phe|Ala
|Leu|Arg 210|Pro|Ala|Pro|Gln|Gly 215|Ile|Thr|Ile|Lys|Cys 220|Arg|Ile|Thr|Arg
|Asp 225|Lys|Lys|Gly|Met|Asp 230|Arg|Gly|Met|Tyr|Pro 235|Thr|Tyr|Phe|Leu|His 240
|Leu|Asp|Arg|Glu|Asp 245|Gly|Lys|Lys|Val|Phe 250|Leu|Leu|Ala|Gly|Arg 255|Lys
|Arg|Lys|Lys|Ser 260|Lys|Thr|Ser|Asn|Tyr 265|Leu|Ile|Ser|Val|Asp 270|Pro|Thr
|Asp|Leu|Ser 275|Arg|Gly|Gly|Asp|Ser 280|Tyr|Ile|Gly|Lys|Leu 285|Arg|Ser|Asn
|Leu|Met 290|Gly|Thr|Lys|Phe|Thr 295|Val|Tyr|Asp|Asn|Gly 300|Val|Asn|Pro|Gln
|Lys 305|Ala|Ser|Ser|Ser|Thr 310|Leu|Glu|Ser|Gly|Thr 315|Leu|Arg|Gln|Glu|Leu 320
|Ala|Ala|Val|Cys|Tyr 325|Glu|Thr|Asn|Val|Leu 330|Gly|Phe|Lys|Gly|Pro 335|Arg
|Lys|Met|Ser|Val 340|Ile|Val|Pro|Gly|Met 345|Asn|Met|Val|His|Gly 350|Glu|Arg|Val
|Cys|Ile|Arg 355|Pro|Arg|Asn|Glu|His 360|Glu|Thr|Leu|Leu|Ala 365|Arg|Trp|Gln
|Asn|Lys|Asn 370|Thr|Glu|Ser|Ile|Ile 375|Glu|Leu|Gln|Asn|Lys 380|Thr|Pro|Val
|Trp 385|Asn|Asp|Asp|Thr|Gln 390|Ser|Tyr|Val|Leu|Asn 395|Phe|His|Gly|Arg|Val 400
|Thr|Gln|Ala|Ser|Val 405|Lys|Asn|Phe|Gln|Ile 410|Ile|His|Gly|Asn|Asp 415|Pro
|Asp|Tyr|Ile|Val 420|Met|Gln|Phe|Gly|Arg 425|Val|Ala|Glu|Asp|Val 430|Phe|Thr
|Met|Asp|Tyr|Asn 435|Tyr|Pro|Leu|Cys 440|Ala|Leu|Gln|Ala|Phe 445|Ala|Ile|Ala
|Leu|Ser 450|Ser|Phe|Asp|Ser|Lys 455|Leu|Ala|Cys|Glu| | | | |

( 2 ) INFORMATION FOR SEQ ID NO:3:

( i ) SEQUENCE CHARACTERISTICS:
        ( A ) LENGTH: 2434 base pairs
        ( B ) TYPE: nucleic acid
        ( C ) STRANDEDNESS: double ( D ) TOPOLOGY: linear ( i i ) MOLECULE TYPE: cDNA ( x i ) SEQUENCE DESCRIPTION: SEQ ID NO:3:

```
CCTCTCCCGA  GCGCTGCACC  GCGCACAGAC  AACCGTTCTG  GGAGCCCGCG  GCCGGGGCCC    60
TGGCGTGCAG  AGAGGGCCTC  GGCGGGGCCC  AGCGGTCGGG  CCGGGGAGGA  TGCGGCCCGG   120
GGCGGCCCGA  GAGTTGAGCA  GGGTCCCCGC  GCCAGCCCCG  AGCGGTCCCG  GCCACCGGAG   180
CCGCAGCCGC  CGCCCCGCCC  CCGGGAGACA  TGACTTCCAA  GCCGCATTCC  GACTGGATTC   240
CTTACAGTGT  CCTAGATGAT  GAGGGCAGCA  ACCTGAGGCA  GCAGAAGCTC  GACCGGCAGC   300
GGGCCCTGTT  GGAACAGAAG  CAGAAGAAGA  AGCGCCAAGA  GCCCTTGATG  GTACAGGCCA   360
ATGCAGATGG  ACGGCCCCGG  AGTCGGCGAG  CCCGGCAGTC  AGAGGAGCAA  GCCCCCCTGG   420
TGGAGTCCTA  CCTCAGCAGC  AGTGGCAGCA  CCAGCTACCA  AGTTCAAGAG  GCCGACTCGA   480
TTGCCAGTGT  ACAGCTGGGA  GCCACCCGCC  CACCAGCACC  AGCCTCAGCC  AAGAAATCCA   540
AGGGAGCGGC  TGCATCTGGG  GGCCAGGGTG  GAGCCCCTAG  GAAGGAGAAG  AAGGGAAAGC   600
ATAAAGGCAC  CAGCGGGCCA  GCAACTCTGG  CAGAAGACAA  GTCTGAGGCC  CAAGGCCCAG   660
TGCAGATCTT  GACTGTGGGA  CAGTCAGACC  ACGACAAGGA  TGCGGGAGAG  ACAGCAGCCG   720
GCGGGGGCGC  ACAGCCCAGT  GGGCAGGACC  TCCGTGCCAC  GATGCAGAGG  AAGGGCATCT   780
CCAGCAGCAT  GAGCTTTGAC  GAGGACGAGG  ATGAGGATGA  AAACAGCTCC  AGCTCCTCCC   840
AGCTAAACAG  CAACACCCGC  CCTAGTTCTG  CCACTAGCAG  AAAGTCCATC  CGGGAGGCAG   900
CTTCAGCCCC  CAGCCCAGCC  GCCCCAGAGC  CACCAGTGGA  TATTGAGGTC  CAGGATCTAG   960
AGGAGTTTGC  ACTGAGGCCA  GCCCCACAAG  GGATCACCAT  CAAATGCCGC  ATCACTCGGG  1020
ACAAGAAGGG  GATGGACCGC  GGCATGTACC  CCACCTACTT  TCTGCACCTA  GACCGTGAGG  1080
ATGGCAAGAA  GGTGTTCCTC  CTGGCGGGCA  GGAAGAGAAA  GAAGAGTAAA  ACTTCCAATT  1140
ACCTCATCTC  TGTGGACCCA  ACAGACTTGT  CTCGGGGAGG  CGATAGCTAT  ATCGGGAAAT  1200
TGCGGTCCAA  CCTGATGGGC  ACCAAGTTCA  CCGTTTATGA  CAATGGCGTC  AACCCTCAGA  1260
AGGCATCCTC  TTCCACGCTG  GAAAGCGGAA  CCTTGCGCCA  GGAGCTGGCA  GCGGTGTGCT  1320
ATGAGACAAA  TGTCCTAGGC  TTCAAGGGAC  CTCGGAAGAT  GAGTGTGATC  GTCCCAGGCA  1380
TGAACATGGT  TCATGAGAGA  GTCTGTATCC  GCCCCCGCAA  TGAACATGAG  ACCCTGTTAG  1440
CACGCTGGCA  GAACAAGAAC  ACGGAGAGCA  TCATTGAGCT  GCAGAACAAG  ACGCCAGTCT  1500
GGAATGATGA  CACACAGTCC  TATGTACTTA  ACTTCCACGG  CCGTGTCACA  CAGGCTTCTG  1560
TGAAGAACTT  CCAGATCATC  CACGGCAATG  ACCCGGACTA  CATCGTCATG  CAGTTTGGCC  1620
GGGTAGCAGA  AGATGTGTTC  ACCATGGATT  ACAACTACCC  ACTGTGTGCA  CTGCAGGCCT  1680
TTGCCATTGC  TCTGTCCAGC  TTTGACAGCA  AGCTGGCCTG  CGAGTAGAGG  CCCCACTGC   1740
CTTTAGGTGG  CCCAGTCCGG  AGTGGAGCTT  GCCTGCCTGC  CAAGACAGCC  CTGCCTACCC  1800
TCTGTTCATA  GGCCCTCTAT  GGGCTTTCTG  GCCTTACCAA  CCAGAGACTG  GCTGCTCTGC  1860
CTCTGCTGCT  GAAGCAGGGG  GGACAGCAAA  TGGGTATGAC  AGGAGAAGAA  TATTTCTGTG  1920
CCCCAAGGTC  AACACACATG  CCCAGTCCTG  GGTCAGTCCC  CTGCTGCAGT  GGTGTTATCA  1980
CACCGGAAAG  CCTCTTCACC  TGGAGGTACA  GAGGGAGAGG  AAGCACAAGC  CTGGCTGCTG  2040
TGGYTCAGCC  ATCCACTCAG  CCTACGAGTC  AGAGACAGTG  GGTGTCCCKG  GAAGCRGGGG  2100
TACAGTGAGT  GTGTGTGTAT  GTACAGGGCA  CTCAAGCTGT  ATGTAGAAAA  AGCTCTGGTG  2160
GTCAGCAGAA  AGCACTCCCR  CTTCAAAAGG  GCCCATTAGG  CCCAAAGGGG  GTTAGGAGTG  2220
```

-continued

```
GTAGGGATAG  GTGCGTGGCA  GGTCCCTGCT  AGGATTGCAG  GGGCCTGGCC  ATGTGTATTA    2280

GCTGGAGGCT  TAGAATGCTA  GCTCATTTGT  TGCTACAGAT  TTGCCCAGTG  CTTGCAYACG    2340

TAAGAACCCA  GCTCTCAAGG  CCAAATATCT  GAKTGGATGG  GGATGATAGG  AGTCATCCAG    2400

TAGACTCCCT  ACATCAGGGC  TCTCAGCAGC  CCCA                                  2434
```

( 2 ) INFORMATION FOR SEQ ID NO:4:

( i ) SEQUENCE CHARACTERISTICS:
        ( A ) LENGTH: 505 amino acids
        ( B ) TYPE: amino acid
        ( C ) STRANDEDNESS: double
        ( D ) TOPOLOGY: linear ( i i ) MOLECULE TYPE: peptide ( x i ) SEQUENCE DESCRIPTION: SEQ ID NO:4:

```
Met  Thr  Ser  Lys  Pro  His  Ser  Asp  Trp  Ile  Pro  Tyr  Ser  Val  Leu  Asp
 1              5                        10                       15

Asp  Glu  Gly  Ser  Asn  Leu  Arg  Gln  Gln  Lys  Leu  Asp  Arg  Gln  Arg  Ala
               20                        25                       30

Leu  Leu  Glu  Gln  Lys  Gln  Lys  Lys  Arg  Gln  Glu  Pro  Leu  Met  Val
          35                        40                       45

Gln  Ala  Asn  Ala  Asp  Gly  Arg  Pro  Arg  Ser  Arg  Arg  Ala  Arg  Gln  Ser
          50                        55                       60

Glu  Glu  Gln  Ala  Pro  Leu  Val  Glu  Ser  Tyr  Leu  Ser  Ser  Ser  Gly  Ser
 65                       70                       75                       80

Thr  Ser  Tyr  Gln  Val  Gln  Glu  Ala  Asp  Ser  Ile  Ala  Ser  Val  Gln  Leu
                    85                        90                       95

Gly  Ala  Thr  Arg  Pro  Pro  Ala  Pro  Ala  Ser  Ala  Lys  Lys  Ser  Lys  Gly
               100                       105                      110

Ala  Ala  Ala  Ser  Gly  Gly  Gln  Gly  Gly  Ala  Pro  Arg  Lys  Glu  Lys  Lys
               115                       120                      125

Gly  Lys  His  Lys  Gly  Thr  Ser  Gly  Pro  Ala  Thr  Leu  Ala  Glu  Asp  Lys
     130                       135                      140

Ser  Glu  Ala  Gln  Gly  Pro  Val  Gln  Ile  Leu  Thr  Val  Gly  Gln  Ser  Asp
145                       150                      155                      160

His  Asp  Lys  Asp  Ala  Gly  Glu  Thr  Ala  Ala  Gly  Gly  Gly  Ala  Gln  Pro
               165                       170                      175

Ser  Gly  Gln  Asp  Leu  Arg  Ala  Thr  Met  Gln  Arg  Lys  Gly  Ile  Ser  Ser
               180                       185                      190

Ser  Met  Ser  Phe  Asp  Glu  Asp  Glu  Asp  Glu  Asn  Ser  Ser  Ser
          195                       200                      205

Ser  Ser  Gln  Leu  Asn  Ser  Asn  Thr  Arg  Pro  Ser  Ser  Ala  Thr  Ser  Arg
     210                       215                      220

Lys  Ser  Ile  Arg  Glu  Ala  Ala  Ser  Ala  Pro  Ser  Pro  Ala  Ala  Pro  Glu
225                       230                      235                      240

Pro  Pro  Val  Asp  Ile  Glu  Val  Gln  Asp  Leu  Glu  Glu  Phe  Ala  Leu  Arg
                    245                       250                      255

Pro  Ala  Pro  Gln  Gly  Ile  Thr  Ile  Lys  Cys  Arg  Ile  Thr  Arg  Asp  Lys
               260                       265                      270

Lys  Gly  Met  Asp  Arg  Gly  Met  Tyr  Pro  Thr  Tyr  Phe  Leu  His  Leu  Asp
          275                       280                      285

Arg  Glu  Asp  Gly  Lys  Lys  Val  Phe  Leu  Leu  Ala  Gly  Arg  Lys  Arg  Lys
     290                       295                      300

Lys  Ser  Lys  Thr  Ser  Asn  Tyr  Leu  Ile  Ser  Val  Asp  Pro  Thr  Asp  Leu
305                       310                      315                      320
```

|  |  |  |  |  |  |  |  |  |  |  |  |  |  |  |
|---|---|---|---|---|---|---|---|---|---|---|---|---|---|---|
| Ser | Arg | Gly | Gly | Asp<br>325 | Ser | Tyr | Ile | Gly | Lys<br>330 | Leu | Arg | Ser | Asn | Leu<br>335 | Met |
| Gly | Thr | Lys | Phe<br>340 | Thr | Val | Tyr | Asp | Asn<br>345 | Gly | Val | Asn | Pro | Gln<br>350 | Lys | Ala |
| Ser | Ser | Ser<br>355 | Thr | Leu | Glu | Ser | Gly<br>360 | Thr | Leu | Arg | Gln | Glu<br>365 | Leu | Ala | Ala |
| Val | Cys<br>370 | Tyr | Glu | Thr | Asn | Val<br>375 | Leu | Gly | Phe | Lys | Gly<br>380 | Pro | Arg | Lys | Met |
| Ser<br>385 | Val | Ile | Val | Pro | Gly<br>390 | Met | Asn | Met | Val | His<br>395 | Glu | Arg | Val | Cys | Ile<br>400 |
| Arg | Pro | Arg | Asn | Glu<br>405 | His | Glu | Thr | Leu | Leu<br>410 | Ala | Arg | Trp | Gln | Asn<br>415 | Lys |
| Asn | Thr | Glu | Ser<br>420 | Ile | Ile | Glu | Leu | Gln<br>425 | Asn | Lys | Thr | Pro | Val<br>430 | Trp | Asn |
| Asp | Asp | Thr<br>435 | Gln | Ser | Tyr | Val | Leu<br>440 | Asn | Phe | His | Gly | Arg<br>445 | Val | Thr | Gln |
| Ala | Ser | Val<br>450 | Lys | Asn | Phe | Gln<br>455 | Ile | Ile | His | Gly | Asn<br>460 | Asp | Pro | Asp | Tyr |
| Ile<br>465 | Val | Met | Gln | Phe | Gly<br>470 | Arg | Val | Ala | Glu | Asp<br>475 | Val | Phe | Thr | Met | Asp<br>480 |
| Tyr | Asn | Tyr | Pro | Leu<br>485 | Cys | Ala | Leu | Gln | Ala<br>490 | Phe | Ala | Ile | Ala | Leu<br>495 | Ser |
| Ser | Phe | Asp | Ser<br>500 | Lys | Leu | Ala | Cys | Glu<br>505 |  |  |  |  |  |  |  |

(2) INFORMATION FOR SEQ ID NO:5:

(i) SEQUENCE CHARACTERISTICS:
        (A) LENGTH: 480 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

| | | | | | |
|---|---|---|---|---|---|
| ACTTCCAGAT | CATCCACGGC | AATGACCTTG | AGTGTTGCCA | CTCCCTGTTT | TTGATGTTGT | 60 |
| ACGCATGGTG | CCCAGCCCCC | ACCCCACCCC | CAATCCCCTG | ATCTGGTCCA | TATCAGCCAG | 120 |
| TGATGGGATG | TGGGTATATG | GCTTTTGTTA | GAACTTTCTA | ACTGTAGTGA | TCTAGAGTCC | 180 |
| TGCCCCTAGT | GCCCTGCATG | TCTGGGGCTT | GGGAATACCC | TTTAAATGGA | TGTCTTTTCT | 240 |
| CTCCTGGGCC | CTGCTGTCTG | TGTGCATCTC | CCCCCTTCAC | CCTCTTGCTT | CATAATGTTT | 300 |
| CTCTTGAACC | TTTGTTTTGT | TCATCCTTTC | GATCTCTTTG | GCATTTCTGC | TTTCTCCTTC | 360 |
| CCTCTTGTGG | CCCATGTCTT | ACCTGGTCTC | CCTGTCTCCA | CCAATTCTTG | CTTGGTGCAT | 420 |
| GCCACAGCGG | ACTACATCGT | CATGCAGTTT | GGCCGGGTAG | CAGAAGATGT | GTTCACCATG | 480 |

(2) INFORMATION FOR SEQ ID NO:6:

(i) SEQUENCE CHARACTERISTICS:
        (A) LENGTH: 1426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

| | | | | | |
|---|---|---|---|---|---|
| CAGAAGAAGA | AGCGCCAGGA | GCCCCTGATG | GTGCAGGCCA | ATGCAGATGG | GCGGCCCCGG | 60 |

| | | | | | |
|---|---|---|---|---|---|
| AGCCGGCGGG | CCCGGCAGTC | AGAGGAACAA | GCCCCCTGG | TGGAGTCCTA | CCTCAGCAGC | 120 |
| AGTGGCAGCA | CCAGCTACCA | AGTTCAAGAG | GCCGACTCAC | TCGCCAGTGT | GCAGCTGGGA | 180 |
| GCCACGCGCC | CAACAGCACC | AGCTTCAGCC | AAGAGAACCA | AGGCGGCAGC | TACAGCAGGG | 240 |
| GGCCAGGGCG | GCGCCGCTAG | GAAGGAGAAG | AAGGGAAAGC | ACAAAGGCAC | CAGCGGGCCA | 300 |
| GCAGCACTGG | CAGAAGACAA | GTCTGAGGCC | CAAGGCCCAG | TGCAGATTCT | GACTGTGGGC | 360 |
| CAGTCAGACC | ACGCCCAGGA | CGCAGGGGAG | ACGGCAGCTG | GTGGGGCGA | ACGGCCCAGC | 420 |
| GGGCAGGATC | TCCGTGCCAC | GATGCAGAGG | AAGGGCATCT | CCAGCAGCAT | GAGCTTTGAC | 480 |
| GAGGATGAGG | AGGATGAGGA | GGAGAATAGC | TCCAGCTCCT | CCCAGCTAAA | TAGTAACACC | 540 |
| CGCCCCAGCT | CTGCTACTAG | CAGGAAGTCC | GTCAGGGAGG | CAGCCTCAGC | CCCTAGCCCA | 600 |
| ACAGCTCCAG | AGCAACCAGT | GGACGTTGAG | GTCCAGGATC | TTGAGGAGTT | TGCACTGAGG | 660 |
| CCGGCCCCCC | AGGGTATCAC | CATCAAATGC | CGCATCACTC | GGGACAAGAA | AGGGATGGAC | 720 |
| CGGGGCATGT | ACCCCACCTA | CTTTCTGCAC | CTGGACCGTG | AGGATGGGAA | GAAGGTGTTC | 780 |
| CTCCTGGCGG | GAAGGAAGAG | AAAGAAGAGT | AAAACTTCCA | ATTACCTCAT | CTCTGTGGAC | 840 |
| CCAACAGACT | TGTCTCGAGG | AGGGGACAGC | TATATCGGGA | AACTGCGGTC | CAACTTGATG | 900 |
| GGCACCAAGT | TCACTGTTTA | TGACAATGGA | GTCAACCCTC | AGAAGGCCTC | ATCCTCCACT | 960 |
| TTGGAAAGTG | GAACCTTACG | TCAGGAGCTG | GCAGCTGTGT | GCTACGAGAC | AAACGTCTTA | 1020 |
| GGCTTCAAGG | GGCCTCGGAA | GATGAGCGTG | ATTGTCCCAG | GCATGAACAT | GGTCCATGAG | 1080 |
| AGAGTCTCTA | TCCGCCCCCG | CAACGAGCAT | GAGACACTGC | TAGCACGCTG | GCAGAATAAG | 1140 |
| AACACGGAGA | GTATCATCGA | GCTGCAAAAC | AAGACACCTG | TCTGGAATGA | TGACACACAG | 1200 |
| TCCTATGTAC | TCAACTTCCA | TGGGCGCGTC | ACACAGGCCT | CCGTGAAGAA | CTTCCAGATC | 1260 |
| ATCCATGGCA | ATGACCCGGA | CTACATCGTG | ATGCAGTTTG | GCCGGGTAGC | AGAGGATGTG | 1320 |
| TTCACCATGG | ATTACAACTA | CCCGCTGTGT | GCACTGCAGG | CCTTTGCCAT | TGCCCTGTCC | 1380 |
| AGCTTCGACA | GCAAGCTGGC | GTGCGAGTAG | AGGCCTCTTC | GTGCCC | | 1426 |

( 2 ) INFORMATION FOR SEQ ID NO:7:

( i ) SEQUENCE CHARACTERISTICS:
        ( A ) LENGTH: 460 amino acids
        ( B ) TYPE: amino acid
        ( C ) STRANDEDNESS: double
        ( D ) TOPOLOGY: linear ( i i ) MOLECULE TYPE: peptide ( x i ) SEQUENCE DESCRIPTION: SEQ ID NO:7:

```
Met  Val  Gln  Ala  Asn  Ala  Asp  Gly  Arg  Pro  Arg  Ser  Arg  Arg  Ala  Arg
 1                  5                        10                       15

Gln  Ser  Glu  Glu  Gln  Ala  Pro  Leu  Val  Glu  Ser  Tyr  Leu  Ser  Ser  Ser
               20                       25                       30

Gly  Ser  Thr  Ser  Tyr  Gln  Val  Gln  Glu  Ala  Asp  Ser  Leu  Ala  Ser  Val
          35                       40                       45

Gln  Leu  Gly  Ala  Thr  Arg  Pro  Thr  Ala  Pro  Ala  Ser  Ala  Lys  Arg  Thr
     50                       55                       60

Lys  Ala  Ala  Ala  Thr  Ala  Gly  Gly  Gln  Gly  Gly  Ala  Ala  Arg  Lys  Glu
65                       70                       75                       80

Lys  Lys  Gly  Lys  His  Lys  Gly  Thr  Ser  Gly  Pro  Ala  Ala  Leu  Ala  Glu
                    85                       90                       95

Asp  Lys  Ser  Glu  Ala  Gln  Gly  Pro  Val  Gln  Ile  Leu  Thr  Val  Gly  Gln
               100                      105                      110
```

| | | | | | | | | | | | | | | |
|---|---|---|---|---|---|---|---|---|---|---|---|---|---|---|
| Ser | Asp | His<br>115 | Ala | Gln | Asp | Ala | Gly<br>120 | Glu | Thr | Ala | Ala | Gly<br>125 | Gly | Glu |
| Arg | Pro<br>130 | Ser | Gly | Gln | Asp | Leu<br>135 | Arg | Ala | Thr | Met | Gln<br>140 | Arg | Lys | Gly | Ile |
| Ser<br>145 | Ser | Ser | Met | Ser | Phe<br>150 | Asp | Glu | Asp | Glu | Asp<br>155 | Glu | Glu | Glu | Asn<br>160 |
| Ser | Ser | Ser | Ser | Ser<br>165 | Gln | Leu | Asn | Ser | Asn<br>170 | Thr | Arg | Pro | Ser<br>175 | Ala |
| Thr | Ser | Arg | Lys<br>180 | Ser | Val | Arg | Glu | Ala<br>185 | Ala | Ser | Ala | Pro | Ser<br>190 | Pro | Thr |
| Ala | Pro | Glu<br>195 | Gln | Pro | Val | Asp | Val<br>200 | Glu | Val | Gln | Asp | Leu<br>205 | Glu | Glu | Phe |
| Ala | Leu | Arg<br>210 | Pro | Ala | Pro | Gln<br>215 | Gly | Ile | Thr | Ile | Lys<br>220 | Cys | Arg | Ile | Thr |
| Arg<br>225 | Asp | Lys | Lys | Gly | Met<br>230 | Asp | Arg | Gly | Met | Tyr<br>235 | Pro | Thr | Tyr | Phe | Leu<br>240 |
| His | Leu | Asp | Arg | Glu<br>245 | Asp | Gly | Lys | Lys | Val<br>250 | Phe | Leu | Leu | Ala | Gly<br>255 | Arg |
| Lys | Arg | Lys | Lys<br>260 | Ser | Lys | Thr | Ser | Asn<br>265 | Tyr | Leu | Ile | Ser | Val<br>270 | Asp | Pro |
| Thr | Asp | Leu<br>275 | Ser | Arg | Gly | Gly | Asp<br>280 | Ser | Tyr | Ile | Gly | Lys<br>285 | Leu | Arg | Ser |
| Asn | Leu<br>290 | Met | Gly | Thr | Lys | Phe<br>295 | Thr | Val | Tyr | Asp | Asn<br>300 | Gly | Val | Asn | Pro |
| Gln<br>305 | Lys | Ala | Ser | Ser | Ser<br>310 | Thr | Leu | Glu | Ser | Gly<br>315 | Thr | Leu | Arg | Gln | Glu<br>320 |
| Leu | Ala | Ala | Val | Cys<br>325 | Tyr | Glu | Thr | Asn | Val<br>330 | Leu | Gly | Phe | Lys | Gly<br>335 | Pro |
| Arg | Lys | Met | Ser<br>340 | Val | Ile | Val | Pro | Gly<br>345 | Met | Asn | Met | Val | His<br>350 | Glu | Arg |
| Val | Ser | Ile<br>355 | Arg | Pro | Arg | Asn | Glu<br>360 | His | Glu | Thr | Leu | Leu<br>365 | Ala | Arg | Trp |
| Gln | Asn<br>370 | Lys | Asn | Thr | Glu | Ser<br>375 | Ile | Ile | Glu | Leu | Gln<br>380 | Asn | Lys | Thr | Pro |
| Val<br>385 | Trp | Asn | Asp | Asp | Thr<br>390 | Gln | Ser | Tyr | Val | Leu<br>395 | Asn | Phe | His | Gly | Arg<br>400 |
| Val | Thr | Gln | Ala | Ser<br>405 | Val | Lys | Asn | Phe | Gln<br>410 | Ile | Ile | His | Gly | Asn<br>415 | Asp |
| Pro | Asp | Tyr | Ile<br>420 | Val | Met | Gln | Phe | Gly<br>425 | Arg | Val | Ala | Glu | Asp<br>430 | Val | Phe |
| Thr | Met | Asp<br>435 | Tyr | Asn | Tyr | Pro<br>440 | Leu | Cys | Ala | Leu | Gln<br>445 | Ala | Phe | Ala | Ile |
| Ala | Leu<br>450 | Ser | Ser | Phe | Asp<br>455 | Ser | Lys | Leu | Ala | Cys<br>460 | Glu | | | | |

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:8:

TTCACAAAAG CACACCTGG                                                              1 9

( 2 ) INFORMATION FOR SEQ ID NO:9:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "primer"

( x i ) SEQUENCE DESCRIPTION: SEQ ID NO:9:

GTCCCAAGGA TGGAGACCT                                                              1 9

( 2 ) INFORMATION FOR SEQ ID NO:10:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "primer"

( x i ) SEQUENCE DESCRIPTION: SEQ ID NO:10:

TGGTGAGCAA AACAAGGAAC                                                             2 0

( 2 ) INFORMATION FOR SEQ ID NO:11:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "primer"

( x i ) SEQUENCE DESCRIPTION: SEQ ID NO:11:

TGGGGAAAGC AATTTCTGG                                                              1 9

( 2 ) INFORMATION FOR SEQ ID NO:12:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "primer"

( x i ) SEQUENCE DESCRIPTION: SEQ ID NO:12:

GCCTGTCAGC AAGGACCTT                                                              1 9

( 2 ) INFORMATION FOR SEQ ID NO:13:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "primer"

( x i ) SEQUENCE DESCRIPTION: SEQ ID NO:13:

CCATGTCCCA AACAAGATGG                                                          20

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

ACCTGAGGCA GCAGAAGCT                                                           19

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

CAGCCAGTCT CTGGTTGGT                                                           19

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

TGCAGAACAA GACGCCAGT                                                           19

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:17:

GATGTTGTAC GCATGGTGC                                                           19

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:18:

TGGAGACAGG GAGACCAGG 19

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:19:

GATGGCAAGA AGGTGTTCC 19

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:20:

TCATTGCGGG GGCGGATAC 19

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:21:

ATGGTGAAGG TCGGTGTGAA 20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:22:

ACCAGTAGAC TCCACGACAT 20

(2) INFORMATION FOR SEQ ID NO:23:

(i) SEQUENCE CHARACTERISTICS:
        (A) LENGTH: 171 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:23:

-continued

| | | | | | |
|---|---|---|---|---|---|
| GGTCATTGCC | GTGGATGATC | TGGAAGTTCT | TCACAGAAGC | CTGTGTGACA | CGGCCGTGGA | 60
| AGTTAAGTAC | ATAGGACTGT | GTGTCATCAT | TCCAGACGGC | GTCTTGTTCT | GCAGCTCAAT | 120
| GATGCTCTCC | GTGTTCTTGT | TCTGCCAGCG | TGCTAACAGG | GTCTCATGTT | C | 171

(2) INFORMATION FOR SEQ ID NO:24:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

| | | | | | |
|---|---|---|---|---|---|
| GAGACAAATG | TCCTAGGCTT | CAAGGGACCT | CGGAAGATGA | GTGTGATCGT | CCCAGGCATG | 60
| AACATGGTTC | ATGAGAGAGT | CTGTATCCGC | CCCCGCAAT | | | 99

(2) INFORMATION FOR SEQ ID NO:25:

(i) SEQUENCE CHARACTERISTICS:
        (A) LENGTH: 33 amino acids
        (B) TYPE: amino acid
        (C) STRANDEDNESS: double
        (D) TOPOLOGY: linear (ii) MOLECULE TYPE: peptide (xi) SEQUENCE DESCRIPTION: SEQ ID NO:25:

Asn Phe Gln Ile Ile His Gly Asn Asp Leu Glu Cys Cys His Ser Leu
1               5                   10                  15

Phe Leu Met Leu Tyr Ala Trp Cys Pro Ala Pro Thr Pro Pro Pro Ile
            20                  25                  30

Pro

OBESITY ASSOCIATED GENES

TECHNICAL FIELD

The field of this invention is genes associated with obesity in mammals.

BACKGROUND

Human obesity is a widespread and serious disorder, affecting a high percentage of the adult population in developed countries. In spite of an association with heart disease, type II diabetes, cancer, and other conditions, few persons are able to permanently achieve significant weight loss. Failure to treat obesity may be at least partially attributed to the complexity of the disease. Genetic, psychological and environmental factors all play a role in individual patterns of weight gain or loss, making it exceedingly difficult to define the contribution of any single element.

An understanding of the genetic factors that underlie obesity may aid in treatment. However, defining the exact genetic loci involved in a human polygenic trait requires extensive family studies. Because there are so many genes that can affect the single trait of obesity, in humans it may be virtually impossible to statistically determine the contribution of one locus. An attempt at such mapping studies can be further complicated by the interaction and linkage of genes. Also, environmental effects cannot be assumed to be the same for all genotypes. As an alternative to the complexities of human genetic mapping, animal models may be useful.

Inbred mouse strains are widely used in genetic and immunological studies. Inbred animals are isogenic at all autosomal loci, that is, not only are individuals of the strain genetically identical to each other, but both copies of each diploid gene are also identical. By crossing different inbred strains, it is possible to generate a detailed genetic map of a region. The genetic map can then be used as a basis for physical characterization of the region. However, even the smallest of measurable genetic intervals generally contains somewhere between 5 and 100 different open reading frames. A gene will consist of one or a combination of open reading frames. Each candidate gene must be carefully evaluated for differences between the normal and mutant genotype. Once the mouse gene responsible for the mutant phenotype is identified, it can then be used to identify the human counterpart, and for analysis of the structure and function of the gene product.

Mouse models for obesity include obese (ob), agouti (wt), tubby (tub), fat and diabetes (db). These animal models are extremely useful for their ability to simplify the heritability of an otherwise very complex trait. Molecular characterization of these genetic loci is of great interest for human clinical medicine.

Relevant Literature

The mouse tub mutation is described in Coleman and Eicher (1990) *J Hered* 81:424–7 as an autosomal recessive mutation located on chromosome 7, which causes slowly developing but ultimately severe obesity. Ohlemiller et al. (1995) *Neuroreport* 6:845–9 and Heckenlively et al. (1995) *P.N.A.S.* 92:11100–11104 describe hearing loss and progressive retinal degeneration in tubby mice. The retinal degeration is characterized by loss of photoreceptor cells, resulting in abnormal electroencephalograms by 3 weeks of age. Jones et al. (1992) *Genomics* 14:197–9 localize the tub locus to a specific region of chromosome 7, and demonstrate that it is distinct from the insulin-2 locus. The cholecystokinin receptor gene is shown to tightly linked to the tub locus in Samuelson et al. (1995) *Genome* 6:242–6.

The positional cloning of the mouse ob gene is described in Zhang et al. (1994) *Nature* 372:425–432, and has the Genbank accession number U22421. The mouse agouti gene is described by Miller et al. (1993) *Genes Dev* 7:454–67. The db gene encodes the receptor for the ob gene product, as described in Lee et al. (1996) *Nature* 379:632–635.

SUMMARY OF THE INVENTION

A novel mammalian obesity associated locus is provided as an isolated cDNA, its corresponding genomic sequence, and a purified protein. The locus is also associated with a genetic predisposition to retinal and cochlear degeneration. The nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as treatment of obesity and retinal degeneration, identification of cell type based on expression, and the like. The DNA is further used as a diagnostic for genetic predisposition to obesity.

DESCRIPTION OF THE SPECIFIC EMBODIMENTS

Figure 1:
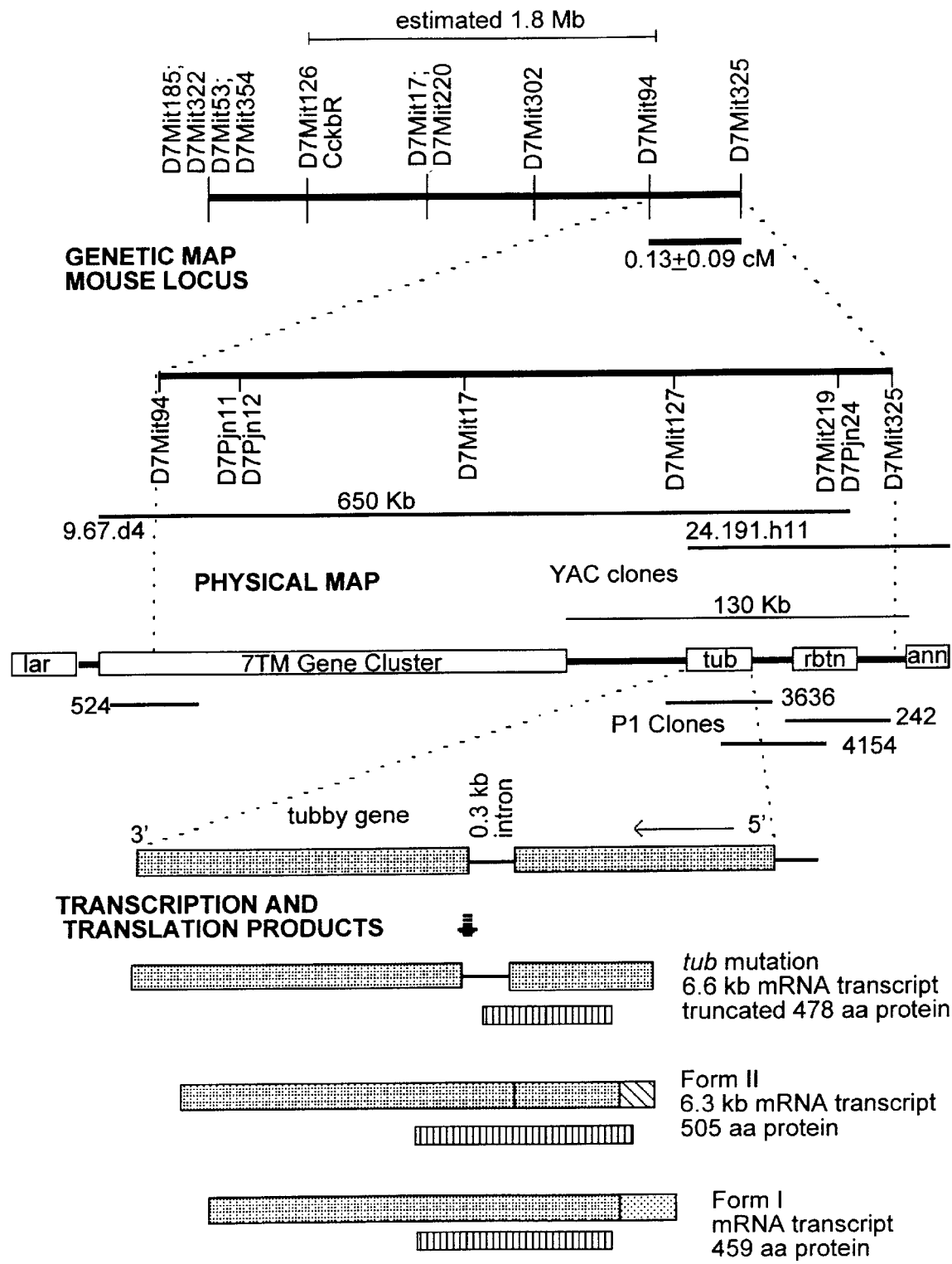
FIG. 1 shows the relationship of physical and genetic maps of the mouse tubby locus, and the transcriptional and translational products of the locus.

Mammalian genes associated with maturity-onset obesity are provided (tubby). Certain individuals having a genetic predisposition to obesity are shown to have a nucleotide sequence in the tubby gene that varies from the wild-type. This genetic variation is also associated with a predisposition to retinal and cochlear degeneration. The sequences of the subject human and mouse homologs are provided. Tubby nucleic acid compositions are used to identify homologous or related genes, to produce the corresponding protein, and in drug screening assays. The DNA is further used as a diagnostic for a specific genetic predisposition to late onset obesity, blindness and deafness.

As used herein, the term tubby designates a coding region, gene or gene product that maps to the exact chromosomal position of the tub mutation described by Coleman and Eicher, supra, and mammalian homologs thereof. The tub mutation confers a genetic predisposition to maturity onset obesity. Various clinical criteria are known in the art for defining morbid obesity in human populations, e.g. having a weight of about 20% above an individual's ideal body weight, etc. The data indicate that the tub mutation is also associated with adult-onset degeneration of the retina and cochlea. The cochlea of affected individuals shows pronounced degeneration of the organ of Corti and loss of afferent neurons in the base, with relative sparing of the apex.

The term tubby encompasses both the normal mammalian sequence and the mutated sequence responsible for the tub phenotype. The gene is expressed at high levels in brain, eye and testis, and at lower levels in various adult and fetal tissues, including small and large intestine, ovary and adipose tissue. Different transcriptional products are formed by alternative exon splicing in the 5' end of the gene.

The wild-type mouse and human tubby cDNA sequences (Form I) are shown in the Sequence Listing as SEQ ID NO:1 and SEQ ID NO:6, respectively. The predicted amino acid sequences for human and mouse are identified as SEQ ID NO:2 and SEQ ID NO:7, respectively. The Form I mouse cDNA encodes a protein of 459 amino acids. The mouse tubby cDNA sequence (Form II) is shown in the Sequence Listing as SEQ ID NO:3. The wild-type Form II mouse cDNA has a 1,584 bp open reading frame, encoding a 505 amino acid protein (SEQ ID NO:4). The mutation in tub/tub mice is a G to T transversion at position 1704 resulting in a splicing defect. The mutated gene sequence (starting at nt 1566 of SEQ ID NO:3) is shown in SEQ ID NO:5, and the predicted protein sequence, which is truncated from the wild-type sequence, is shown in SEQ ID NO:25 (starting from amino acid 453 of SEQ ID NO:4). FIG. 1 shows the different transcriptional and translational products of the tubby gene.

Identification of tubby homologs is based on similarity of sequence, chromosomal synteny, or both. The term homology is used to indicate a likeness of structure and conservation of biological function. Calculations of nucleic acid or amino acid sequence identity, as described below, provide a convenient method of identifying homologous or related genes, herein "homologs". Such homologs may be members of a gene family present in the same genome, or may be corresponding genes from different species. Chromosomal synteny may be used to further distinguish between homologous genes when there is sufficient evolutionary conservation between the genomes that are being compared, e.g. between mammalian species. A "syntenic homolog" has both sequence identity to the reference gene, and has the corresponding chromosomal location in relation to closely linked genes. As an example, the nucleic acid sequences of SEQ ID NO:1 and SEQ ID NO:6 are syntenic homologs. Syntenic homologs have a high probability of sharing spatial and temporal localization of gene expression, and of encoding proteins that fill equivalent biological roles.

The "tubby gene" shall be intended to mean the open reading frame encoding specific polypeptides, as well as adjacent 5' and 3' non-coding nucleotide sequences involved in the regulation of expression of the protein, and will include up to about the length of the mature mRNA. Typically an mRNA sequence will have a continuous open reading frame encoding the desired polypeptide.

The term "cDNA" as used herein is intended to include all nucleic acids that share the arrangement of sequence elements found in native mRNA species, where sequence elements may be exons, 3' and 5' non-coding regions and introns. Normally mRNA species have contiguous exons, with the intervening introns deleted. However, some mutations, e.g. tub, result in abberrant splicing and inclusion of intron sequence in the mature mRNA.

Under some conditions it has been found that a genomic sequence is preferable to a cDNA sequence for expression. In most mammalian genes the genomic sequence will have non-contiguous open reading frames, where introns interrupt the coding regions. A genomic sequence of interest comprises the nucleic acid present between the initiation codon and the stop codon, as defined in the listed sequences, including all of the introns that are normally present in a native chromosome. It may further include the 3' and 5' untranslated regions up to the length of the mature mRNA. It may further include specific transcriptional and translational regulatory sequences, such as promoters, enhancers, etc., up to about 1 kb of flanking genomic DNA at either the 5' or 3' end of the coding region.

A preferred genomic sequence will lack those sequences that are linked to tubby in a native chromosome but which do not contribute to the biological function of the tubby gene. Such sequences are conveniently identified through their relationship to polymorphic markers, as described in Dietrich et al. (1996) *Nature* 380:149 and Dib et al. (1996) *Nature* 380:152. The mouse genomic tubby sequence will typically lack the polymorphic markers D7Mit94, D7Mit17, and D7Mit325. The human tubby sequence will typically lack the polymorphic markers D11S909 and D11S1331.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 35 nt. Such small DNA fragments are useful as primers for PCR, hybridization screening, etc. For use in amplification reactions, such as PCR, a pair of primers will be used. The exact composition of the primer sequences is not critical to the invention, but for most applications the primers will hybridize to the subject tubby sequence under stringent conditions. Conditions for stringent hybridization are known in the art, for example one may use a solution of 5×SSC and 50% formamide, incubated at 42° C. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA sequences are obtained in substantial purity, generally as a sequence other than a sequence of an intact mammalian chromosome. Usually, the DNA will be obtained substantially free of other nucleic acid sequences that do not include an tubby sequence or fragment thereof, generally being at least about 50%, usually at least about 90% pure and are typically "recombinant", i.e. flanked by one or more nucleotides with which it is not normally associated on a naturally occurring chromosome.

The DNA sequences may be used in a variety of ways. They may be used as probes for identifying other tubby polypeptides, including homologs and syntenic homologs. Mammalian homologs have substantial sequence similarity to the subject sequences, i.e. at least 80%, preferably at least 90%, more preferably at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithims for sequence analysis are known in the art, and include BLAST, described in Altschul et al. (1990) *J Mol Biol* 215:403–10; ADVANCE and ADAM, described in Torelli and Robotti (1994) *Comput Appl Biosci* 10:3–5; and FASTA, described in Pearson and Lipman (1988) *P.N.A.S.* 85:2444–8.

Nucleic acids having sequence similarity are detected by hybridization under low stringency conditions, for example, at 50° C. and 10×SSC (0.9M saline/0.09M sodium citrate) and remain bound when subjected to washing at 55° C. in 1×SSC. By using probes, particularly labeled probes of DNA sequences, one can isolate homologous or related genes. The source of homologous genes may be any mammalian species, e.g. primate species, particularly human; murines, such as rats and mice, canines, felines, bovines, ovines, equines, etc.

The DNA sequences, including 5' non-translated sequences, may be used as antisense sequences. Various derivatives of the antisense sequence may be prepared, where the phosphates may be modified, where oxygens may be substituted with sulfur and nitrogen, the sugars may be modified, and the like. The antisense sequences may be used by themselves or in conjunction with various toxic moieties, such as metal chelates, sensitizers, ribozymes, and the like. Antisense sequences may be used to study the effect of tubby loss of function.

The DNA may also be used to identify expression of the gene in a biological specimen. The manner in which one probes cells for the presence of particular nucleotide sequences, as genomic DNA or RNA, is well-established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose and then probed with a fragment of the subject DNA as a probe. Other techniques may also find use. Detection of mRNA having the subject sequence is indicative of tubby gene expression in the sample.

The tubby nucleic acid sequence is used to diagnose a genetic predisposition to obesity, blindness or deafness by analysis of germline DNA for a predisposing mutation, where presence of the altered gene confers an increased susceptibility to one or more of these conditions. Predisposing mutations alter the normal function of tubby. Individuals are screened by analyzing their germline gene sequence for the presence of a predisposing mutation, as compared to a normal sequence. A "normal" sequence of tubby is provided in SEQ ID NO:1 and SEQ ID NO:3 (mouse) and SEQ ID NO:6 (human). The normal tubby sequence shall be understood to include sequence variants in non-coding regions that do not affect the level of expression of the gene, coding region variants that do not change the amino acid sequence, e.g. "third position" changes, and changes that result in an altered amino acid sequence but maintain substantially all of the normal protein function.

Predisposing mutations may occur in the control regions of the gene, where expression of the tubby gene is altered. Alternatively, the mutations will be found in the coding region of the gene, and will change the amino acid sequence of the protein, particularly the active site. Of particular interest are mutations in the splice donor or acceptor sites. In one embodiment of the invention, the predisposing mutation is at nucleotide 1704 of the tubby cDNA (SEQ ID NO:5), resulting in loss of a donor splice site.

The effect of a sequence variation on tubby gene expression or function is determined by kindred analysis for segregation of the sequence variation with the disease phenotype. The subject mutations generally have a recessive phenotype.

As an alternative to kindred studies, biochemical studies are performed to determine whether a candidate sequence variation in the tubby coding region or control regions affects the quantity or function of the protein. For example, a change in the promoter or enhancer sequence that down-regulates expression of tubby may result in disease predisposition. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, chloramphenical acetyltransferase, etc. that provides for convenient quantitation; and the like.

A number of methods are used to determine the presence of a predisposing mutation in an individual. Genomic DNA is isolated from the individual or individuals that are to be tested. DNA can be isolated from any nucleated cellular source such as blood, hair shafts, saliva, mucous, biopsy, feces, etc. Methods using PCR amplification can be performed on the DNA from a single cell, although it is convenient to use at least about $10^5$ cells.

A number of methods are available for analyzing genomic DNA sequences. Where large amounts of DNA are available, the genomic DNA is used directly. Alternatively, the region of interest is cloned into a suitable vector and grown in sufficient quantity for analysis, or amplified by conventional techniques. Of particular interest is the use of the polymerase chain reaction (PCR) to amplify the DNA that lies between two specific primers. The use of the polymerase chain reaction is described in Saiki, et al. (1985) *Science* 239:487, and a review of current techniques may be found in Sambrook, et al. *Molecular Cloning: A Laboratory Manual*, CSH Press 1989, pp.14.2–14.33.

A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high afifnity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to the normal tubby sequence. Alternatively, where the predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilised on a solid support, as described in WO 95/11995, may also be used as a means of detecting the presence of variant sequences.

The subject nucleic acids can be used to generate transgenic animals or site specific gene modifications in cell lines. The modified cells or animals are useful in the study of tubby function and regulation. For example, a series of small deletions or substitutions may be made in the tubby gene to determine the role of different coding regions in obesity, signal transduction, substrate binding, etc.

DNA constructs for homologous recombination will comprise at least a portion of the tubby gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the modified tubby gene and males and females having the modification are mated to produce homozygous progeny. The transgenic animals may be any non-human mammal, such as laboratory animals, domestic animals, etc. The transgenic animals may be used to determine the effect of a candidate drug on obesity or retinal and cochlear degeneration in an in vivo environment.

Investigation of gene function may also utilize non-mammalian models, particularly using those organisms that are biologically and genetically well-characterized, such as *C. elegans, D. melanogaster* and *S. cerevisiae*. The subject gene sequences may be used to complement defined genetic lesions in order to determine the physiological and biochemical pathways involved in tubby function. A number of human genes have been shown to complement mutations in lower eukaryotes. Drug screening may be performed in combination with complementation studies. Many mammalian genes have homologs in yeast and lower animals. The study of such homologs' physiological role and interactions with other proteins can facilitate understanding of biological function. In addition to model systems based on genetic complementation, yeast has been shown to be a powerful tool for studying protein-protein interactions through the two hybrid system described in Chien et al. (1991) *P.N.A.S.* 88:9578–9582.

To produce tubby protein the DNA sequences are expressed by insertion into an appropriate expression vector, where the native transcriptional initiation region may be employed or an exogenous transcriptional initiation region, i.e. a promoter other than the promoter which is associated with the gene in the normally occurring chromosome. The promoter is operably linked to the coding sequence of the tubby gene to produce a translatable mRNA transcript. The promoter may be introduced by recombinant methods in vitro, or as the result of homologous integration of the sequence into a chromosome. A wide variety of constitutive or inducible promoters are known for a wide variety of expression hosts, where the expression hosts may be prokaryotes or eukaryotes, particularly *E. coli; B. subtilis*; yeast cells; mammalian cells; e.g. Cos cells, HeLa cells, L(tk-), primary cultures; insect cells; *Xenopus laevis* oocytes; and the like. Many strong promoters for mammalian cells are known in the art, including the β-actin promoter, SV40 early and late promoters, immunoglobulin promoter, human cytomegalovirus promoter, retroviral LTRs, etc.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the tubby gene or fragment thereof, and a transcriptional termination region. Of particular interest is the use of sequences that allow for the expression of functional epitopes or domains, usually at least about 24 nucleotides in length, more usually at least about 48 nucleotides in length, and up to the complete open reading frame of the gene. After introduction of the DNA, the cells containing the construct may be selected by means of a selectable marker, the cells expanded and then used for expression.

The expression cassettes may be introduced into a variety of vectors, e.g. plasmid, BAC, YAC, bacteriophage such as lambda, P1, M13, etc., animal or plant viruses, and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high-copy copy number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, e.g. conjugation, bacterial transformation, calcium-precipitated DNA, electroporation, fusion, transfection, infection with viral vectors, biolistics, etc.

The DNA sequence may encode amino acid sequences that differ from the native sequence of a tubby polypeptide. The sequence may encode polypeptide analogs, fragments or derivatives of substantially similar polypeptides that differ from the naturally-occurring forms in terms of the identity of location of one or more amino acid residues (deletion analogs containing less than all of the residues specified for the protein, substitution analogs wherein one or more residues are replaced by other residues and addition analogs wherein one or more amino acid residues are added to a terminal or medial portion of the polypeptides) and which share some or all of the properties of naturally-occurring forms. Of particular interest are mutations that confer a genetic predisposition to obesity, and/or retinal and cochlear degeneration.

Sequence analogs include the incorporation of preferred codons for expression in non-mammalian host cells; the provision of sites for cleavage by restriction endonuclease enzymes; the addition of promoters operatively linked to enhance RNA transcription; and the provision of additional initial, terminal or intermediate DNA sequences that facilitate vector construction.

With the availability of the protein in large amounts by employing an expression host, the protein may be isolated and purified in accordance with conventional ways. A lysate may be prepared from the expression host and purified using HPLC, exclusion chromatography, gel electrophoresis, affinity chromatography, or other purification techniques as known in the art. The purified protein will generally be at least about 80% pure, preferably at least about 90% pure, and may be up to 100% pure. By pure is intended free of other proteins, as well as cellular debris.

The polypeptide may be used for the production of antibodies. Antibodies are prepared in accordance with conventional methods, where the expressed polypeptide or protein is used as an immunogen, by itself or conjugated to known immunogenic carriers, e.g. KLH, BSA, etc. Various adjuvants may be employed, as appropriate. For monoclonal antibodies, after one or more booster injections, the spleen of the immunized animal is isolated, the splenocytes immortalized, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y, 1988. The antibodies find use in diagnostic assays for detection of the presence of tubby in patient samples.

By providing for the production of large amounts of tubby protein, one can identify ligands or substrates that bind to, or modulate the action of tubby. The purified protein may be used for determination of three-dimensional crystal structure, which can be used for modeling intermolecular interactions. The subject polypeptides or functional domains thereof are used to screen for agonists or antagonists that modulate the interaction of tubby with its normal substrate, or proteins with which tubby interacts in a normal cell. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like.

The term "agent" as used herein describes any molecule, protein, or pharmaceutical with the capability of directly or indirectly altering the physiological function of tubby. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

The mixture of components are added in any order that provides for the requisite binding. Incubations are performed at any temperature that facilitates optimal activity, typically between 4° and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of obesity, retinal degeneration or cochlear degeneration attributable to a defect in tubby function. The inhibitory agents may be administered in a variety of ways, orally, parenterally e.g. subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The present data suggest that the tubby protein is a phosphodiesterase, which is associated with degeneration of specific neurons in the retina, cochlea and pituitary/hypothalamus region. The histology is consistent with apoptosis of the affected neurons. The cluster of defects present in the tubby phenotype, i.e. adult onset obesity, blindness and deafness, may be accounted for by highly specific neuronal cell death that is triggered by either the expression of a mutated tubby gene product or by the lack of functional wild-type tubby protein. This is supported by an observation of specific hypothalamus and pituitary neuron death in several different strains of mice that are genetically predisposed to obesity. Increased body weight with age may therefore be a result of degeneration in brain areas regulating food intake and energy expenditure.

The availability of the subject gene sequences provides a means of analyzing the biology and biochemistry of obesity and specific neural degeneration through in vitro and in vivo drug screening, the use of transgenic animals, complementation of specific genetic lesions, etc., as previously described.

Two pathways of particular interest are apoptosis in neural cells and heterotrimeric G-protein signaling. Both systems may interact to produce the tubby phenotype. It is known that light activated retinal cyclic GMP phosphodiesterases (PDE) (for example, Genbank accession nos. M26061, X62692-X62695, X55968, M36476 and Y00746) play a critical role in visual signal transduction by linking effector and second messenger systems. These PDEs are activated by heterotrimeric G proteins to hydrolyze cyclic GMP to 5'-GMP, thereby regulating ion channels or other effector systems. Mutations in the β subunit of cGMP phosphodiesterase cause retinal degeneration in mice with the rd1 mutation and in humans, and in rd1/rd1 mice an abnormal accumulation of cGMP appears to trigger apoptosis of the photoreceptor cells.

Drug screening assays may be performed with mutant and wild-type tubby protein to detect agents that act as agonists or antagonists for tubby function. The interaction of tubby with other proteins in these pathways is of particular interest, and may be detected in a variety of assays, e.g. yeast two hybrid system, in vitro protein-protein binding assays, genetic complementation, etc. There are a number of characterized genes and gene products that operate to regulate or effect apoptosis and G-protein signaling.

Complementation in animal and yeast models is particularly useful in the study of apoptosis. The genetics of programmed cell death has been well-defined in several animal models. Both C. elegans and D. melanogaster regulate apoptosis through the expression of two gene products, ced-3 and ced-9, and rpr and hid, respectively. The relative simplicity of these pathways is attractive for biochemical and genetic analysis. Both animals are used as screening tools in conjunction with the subject gene sequences, and with their corresponding tubby homologs.

A number of apoptotic and anti-apoptotic genes are expressed in the brain, and may be involved in neural degeneration. Neurons depend on factors such as nerve growth factor and brain derived neurotrophic factor for survival, and may undergo apoptosis where the factor or its receptor are mutated. Among the anti-apoptotic genes of interest are bcl-2, bcl-xL and mcl-1. Inducers of apoptosis include fas (CD95), myc, bax, bcl-xs, TNF receptor and the family of cysteine proteases that includes interleukin 1 β-converting enzyme.

Drug screening assays of interest also include agonists and antagonists of heterotrimeric G protein signaling. Of particular interest are agents that are competitors or enhancers of certain drugs known to promote weight loss, including agents that act at adrenergic receptors in the brain, e.g. sympathomimetic amines and agents that act at serotonergic receptors, e.g. fenfluramine and fluoxetine. The sympathomimetic amines include phentermine (Fastin/SmithKline Beecham), mazindol (Sanorex/Sandoz, Mazanor/Wyeth-Ayerst), diethylpropion (Tenuate/Marion Merrell Dow), and phenylpropanolamine. Also of interest are agonists and antagonists of sibutramine, a monoamine that blocks the reuptake of norepinephrine and, to a lesser extent, serotonin and dopamine.

The following examples are offered by way of illustration and not by way of limitation.

EXPERIMENTAL

EXAMPLE I

Identification of the Mouse Tubby Gene

The tubby mutation arose spontaneously in the C57BL/6J mouse strain. Homozygotes are recognizable by increased body weight at 3 to 4 months in males and at 4 to 6 months in females. Both sexes are fertile. The increased weight is composed of excess adipose tissue. Blood glucose is normal, but plasma insulin is increased prior to obvious signs of obesity and may rise to 20 times normal by 6 months. The islets of Langerhans are moderately enlarged with signs of hyperactivity and the mice display early onset retinal degeneration leading to blindness.

Materials and Methods

Genetic mapping of the tub locus. DNA samples isolated from the progeny of crosses between C57BL16-tub/tub, CAST/Ei, AKR or NOD NON-H2K[b] were genotyped for simple sequence length polymorphisms (Dietrich et al. (1994) Nature Genet. 7:220–245). All recombinants were progeny tested with a minimum of 20 offspring to confirm phenotypic classification. PCR amplification was performed as described in Naggert et al. (1995) Nature Genet. 10:135–141. The amplification primers used were as follows:

| Marker | Forward Primer | Reverse Primer |
| --- | --- | --- |
| D7Pjn11 | SEQ ID NO: 8<br>TTCACAAAAGCACACCTGG | SEQ ID NO: 9<br>GTCCCAAGGATGGAGACCT |
| D7Pjn12 | SEQ ID NO: 10<br>TGGTGAGCAAAACAAGGAAC | SEQ ID NO: 11<br>TGGGGAAAGCAATTTCTGG |
| D7Pjn24 | SEQ ID NO: 12<br>GCCTGTCAGCAAGGACCTT | SEQ ID NO: 13<br>CCATGTCCCAAACAAGATGG |

YAC clones were obtained by PCR screening of mouse YAC DNA pools from Research Genetics, Inc. (Huntsville, Ala.) and P1 clones were obtained from Genome Systems (St. Louis, Mo.). Briefly, DNA from YAC or P1 pools was used as a template in PCR with a specific primer pair as shown above. Only pools comprising a YAC or P1 that contains the sequence tag defined by the primer pair will yield an amplification product. Then the process is repeated with the subpools corresponding to the positive superpools. In the YACS this process is continued until a single positive YAC can be identified. In the case of P1s, no subpools for the secondary pools exist, so that the secondary pools are plated, transferred to nylon filter and screened with the labeled sequence tag obtained with the specific primer pair. A positive P1 pool is then isolated.

Additional P1 and cosmid clones were made from YAC967d4, which spans most of the minimal genetic interval, and were used in direct cDNA selection against cDNA from adult testis, brain and eye of C57BL/6 mice. Ten randomly chosen cosmids were used in the cDNA selection. P1s used include 3636, 1848, 2617, Y, 14.6, 4171, 17.12, 4154, and 24.2. cDNAs for selection were a mixture obtained from testis, brain and eye mRNA. The selection was carried out as described by Lovett, *Current protocols in Human Genetics* (eds. Dracopoli et al.) 6.3.1–13 (Current Protocols, NY 1994) and modified by Segre et al. (1995) *Genomics* 28:549–559.

mRNA preparation. Whole organs from C57BL/6J and C57BL/6-tub/tub were flash frozen in liquid nitrogen, homogenized in 500 mM NaCl, 10 mM Tris pH 7.2, 10 mM EDTA, 2% SDS and incubated with 250 $\mu$g/ml proteinase K (EM Sciences, Gibbstown, N.J.) for 2 hours at 37° C. Oligo-dT cellulose (Pharmacia, Piscataway, N.J.) was added to the homogenate, placed on a shaking incubator for several hours and loaded onto PolyPrep chromatography column (BioRad, Richmond, Calif.). After washing in 100 mM NaCl, 10 mM Tris, pH 7.2, 0.1 mM EDTA, poly $A^+$ RNA was eluted in 10 mM Tris pH 7.2, 10 mM EDTA.

Northern blot analysis. 2–5 $\mu$g poly $A^+$ RNA was fractionated on a 1% agarose-formaldehyde gel, transferred to Hybond $N^+$ membrane (Amersham) and hybridized with the indicated probes in the presence of 500 mM NaPO4, 7% SDS, 1 mM EDTA at 65° C. Blots were washed in 40 mM NaPO4, 1% SDS, 1 mM EDTA at 65° C., followed by a stringent wash in 0.1%SDS, 0.1xSSC at 68° C. Integrity, equal loading and transfer efficiency were assessed by control hybridization with a rat GAPDH probe.

An intron specific probe was generated by amplification of genomic PCR product of C13F2 and C13R with oligonucleotide primers C13F3 and C13R3. Nested PCR was used to generate the intron specific fragment in order to obtain a cleaner probe. Probe C15 was obtained by EcoRI digestion of the cDNA clone c15 from the cDNA selection. Probes were random labeled with 32P[$\alpha$dCTP] (Amersham, Arlington Heights, Ill.). Genomic DNA was PCR amplified with oligonucleotide primers flanking the donor splice site, C13F2 and C13R, and was gel purified and manually sequenced by dideoxy cycle sequencing (Sequitherm, Epicentre Technologies, Madison, Wis.). Primer 2.61 F1 was used with C1 3R to obtain a probe DNA fragment for northern blots by amplifying cDNA. Probes were generated by random hexamer priming, as described by Sambrook et al., supra.

| Primers | |
|---|---|
| 2.61F | [SEQ ID NO: 14] ACCTGAGGCAGCAGAAGCT |
| C13R | [SEQ ID NO: 15] CAGCCAGTCTCTGGTTGGT |
| C13F2 | [SEQ ID NO: 16] TGCAGAACAAGACGCCAGT |
| C13F3 | [SEQ ID NO: 17] GATGTTGTACGCATGGTGC |
| C13R3 | [SEQ ID NO: 18] TGGAGACAGGGAGACCAGG |

Reverse transcription-PCR. RT-PCR was performed with RNA from adult tissues using primers 2.40R and 2.40F (specific to nucleotides 1080 and to 1423) or GAPDH. The tub gene specific primers span two introns with a combined length of about 1 kb. Two $\mu$g poly A+ RNA were treated with DNAse I (Boehringer Mannheim, Indianapolis, Ind.) and reverse transcribed using Superscript™ Preamplification System (Gibco/BRL, Gaithersburg, Md.). PCR was performed using 1-10 ng sscDNA, primer 2.40F [SEQ ID NO:19]GATGGCAAGAAGGTGTTCC and 2.40R [SEQ ID NO:20]TCATTGCGGGGGCGGATAC and AmpliTaq™ (Perkin Elmer, Calif.) under the following conditions: 95° C. 1 min denaturation, 94° C. 20 sec, 58° C. 20 sec, 72° C. 30 sec for 49 cycles followed by 72° C. 2 min. Forward and reverse GAPDH oligomers were [SEQ ID NO:21] ATGGTGAAGGTCGGTGTGAA and [SEQ ID NO:22] ACCAGTAGACTCCACGACAT, respectively. The amplification products were electrophoresed in 1% agarose gel, transferred to Hybond N+ (Amersham) and hybridized with either exon or GAPDH cDNA probes.

cDNA library screening. A mouse testis cDNA library from mouse strain CD-1 (Stratagene, La Jolla, Calif.) inserted into lambda UNI-ZAP XR was screened according to the manufacturer's instructions with the 1.6 kb 2.61F-C13R PCR probe, identifying 24 plaques, two of which were purified and sequenced automatically (Prism, Applied Biosystems, Foster City, Calif.). Clone length was between 1 and 2.5 kb. The coding region cDNA sequence of Form I is described in the sequence listing, SEQ ID NO:1. The predicted amino acid sequence is SEQ ID NO:2. The coding region cDNA sequence of Form II is described in the sequence listing SEQ ID NO:3, the predicted amino acid sequence is SEQ ID NO:4.

Results

Genetic Mapping. Tubby was previously mapped in an interspecific (CS1BL/6-tub/tub X CAST/Ei)$F_1$ intercross to 2.4±1.4 cM from Hbb. Markers across a 20 cM interval encompassing Hbb were tested to identify areas of recombination and to define more closely the minimal tub region, using the DNA from the cross described above. Three mapping crosses were used to refine the minimal region containing the gene to between markers D7Mit94 and D7Mit325. FIG. 1 shows genetic and physical maps of the mouse tub region.

A total of 1468 meioses were tested in mapping outcrosses with CAST/Ei. 60 microsatellite markers were used, 91% of which were polymorphic between B6 and CAST. The minimal region containing tub identified by the CAST/Ei outcrosses was between markers D7Mit124 and D7Mit328 with a genetic distance of 0.27±0.14 cM.

In the NOD.NON-H2K$^b$ intercross with C57BL/6 tub/tub, 820 mice or 1640 meioses were tested. Initially, 680 meioses were tested proximally with D7Mit185 and distally with D7Mit130. As a narrower region was identified, 458 and 502 meioses were tested with proximal markers, D7Mit126 and D7Pjn2, respectively. Of 44 markers contained within the largest interval tested, 34 (77%) were polymorphic between C57BL-tub/tub and NOD.NON-H2K$^b$. Overall, 20 recombinant mice were identified in this intercross. The minimal region containing tub lay between markers D7Mit219 and D7Mit130 with a genetic distance of 0.18±0.11 cM.

775 F$_2$ progeny, or 1550 meioses, were tested with D7Mit126 and D7Mit130 as the flanking markers in the (C57BL/6-tub/tub × AKR)F$_1$ intercross. Only nine of the 34 markers mapping to this region were polymorphic between these parentals. The minimal genetic interval containing tub, between D7Pjn12 and D7Mit328, corresponds to a distance of 0.19±0.11 cM.

Physical Mapping. A YAC contig was established spanning the minimal genetic region, establishing order and distance for those markers not separated by recombinants. The minimal genetic interval was shown to be flanked by crossovers at D7Mit94 and D7Mit325, which could be mapped within P1 clones 524 and 242, respectively. The location of the tub gene relative to each crossover was unambiguously determined by progeny testing. Animals carrying crossovers in the region were mated to tub/tub homozygotes and the progeny examined for the tubby phenotype (50% tubby if the crossover chromosome still contained the tubby gene, 0% tubby if the crossover chromosome had lost the tubby gene).

Both flanking markers were shown to map within YAC67d4, giving a maximal physical separation of 650 kb. A high resolution physical map of the region was constructed by P1, BAC and cosmid assembly using STSs derived from end sequencing P1s, by subcloning and sequencing cosmid pools derived from YAC 132b11 (1 Mb, non-chimaeric) and by searching public databases.

Selected 0.6–1.5 kb cDNA clones were sequenced and analyzed for similarities to known sequences in GenBank using the BLASTN program (described in Altshul et al. (1990) J. Mol. Bio. 215:403–410), and for overlaps using the AssemblyLIGN program (Kodak, N.Y.). Unique cDNA clones and single clones from groups of overlapping clones were hybridized to Southern blots of EcoRi digested P1 DNA. Positive clones that mapped to the minimal region were analyzed for genomic alterations and aberrant expression between C57BL/6 and C57BL16-tub/tub mice by Southern and northern blot analysis.

One cDNA clone, c33, from a DNA contig of 12 overlapping sequences, showed an altered hybridization pattern in tubby derived mRNA when compared to C57BL/6. Tubby mice express a slightly larger transcript in brain and testis, 6.6 kb vs. 6.3 kb. Furthermore, clone c33 identified a 2.1 kb transcript in tubby derived mRNA that is not observed in C57BL/6.

To determine the molecular basis of these differences, oligonucleotide primers were made according to the cDNA sequences from the contig of overlapping clones and used to PCR amplify gene specific fragments from cDNA and genomic DNA. Several oligonucleotide combinations derived from the carboxyterminal portion of the gene, as described above, generated an amplification product from tubby derived cDNA that was 300 bp longer than from C57BL/6 cDNA. The genomic nucleotide sequence was compared, and it was found that there was a G to T transversion in the tubby donor splice site, changing the wild-type donor splice site consensus sequence from GTGAGT to TTGAGT. To confirm that the larger transcript observed in tub was due to the presence of this unspliced carboxy terminal intron, a PCR generated probe specific for the intron was hybridized to a northern blot. The probe detected a transcript only in the tubby mRNA, but not in wild-type. Comparison of the sequence surrounding this donor splice site in standard inbred strain from historically independent lineages, AKR/J, BALB/cJ, DBA/2J, two wild-derived strains, CZECHII/Ei and SKIVE/Ei, as well as from rabbit and rat, showed conservation of the C57BL/6 sequence, suggesting that the nucleotide change is not a normal allelic form, but a mutation leading to the abnormal transcripts. The 2.1 kb transcript is likely to arise from truncation of the full length transcript by introduction of a polyadenylation site contained in the unspliced intron. This is supported by hybridization analysis with a sequence 3' of the unspliced intron, which does not hybridize to the 2.1 kb transcript.

Northern blot analysis of adult tissues shows strong expression of tubby in brain, eye and testis. Using a more sensitive RT-PCR assay, gene expression was also detected in the small and large intestine, ovary and adipose tissue of adult mice.

To assemble a full-length cDNA, 24 clones were isolated from a mouse testis oligo-dT primed cDNA library (Stratagene, La Jolla, Calif.). Two forms were identified. The sequence of Form I (SEQ ID NO:1) from nt 393–2579 is identical to Form II (SEQ ID NO:3) from nt 248–2434. The 5' end of the coding regions differ, resulting in a Form I protein that is 46 amino acids shorter than Form II.

The predominantly hydrophilic nature of the predicted amino acid sequence, and absence of a signal sequence, suggest a cytosolic localization for the protein. The carboxy terminal 260 amino acids show a strong similarity (62% identity) to a putative mouse testis-specific phosphodiesterase (GenBank accession number X69827), as well as the C. elegans 48.2K protein (GenBank Q09306, 59% identity). The aminoterminal portion of the tubby gene shows no similarity to any known protein in database searches (BLASTP).

EXAMPLE II

Characterization of the Human Tubby Gene

The human tubby gene was isolated from a human cDNA library by the following methods.

A cDNA library generated from human brain mRNA and cloned into lambda gt11 (Clontech, Palo Alto, Calif.) was used to isolate the human tubby gene. The phage library was plated at 1.2×10$^6$ pfu/plate onto E. coli Y1 090 in standard bacterial medium. The plates were incubated for 9 hours at 37° C. Two nitrocellulose filters were lifted from each plate as described in Sambrook et al., supra., pp.2.114. The filters were hybridized in 10% dextran sulfate, 1% SDS, 1M NaCl, 100 μg/ml salmon testes DNA and the $^{32}$P labeled probes described below, at 65° C. for 16 hr.

The hybridization probes are PCR amplification products of cDNA sequences isolated by exon trapping with the P1 clone 3636, as described in Example 1. The cDNA sequences were cloned into the pSPL3b vector (BRL, Bethesda, Md.) and amplified according to the manufacturer's instructions. A 171 bp probe was generated having the sequence of SEQ ID NO:23, and a 99 bp probe was generated having the sequence of SEQ ID NO:24. The DNA was labeled by random hexamer priming, as described in Example 1.

After hybridization, the filters were washed at 65° C. in a buffer of 2×SSC, 0.1% SDS for 45 min, followed by two washes in 0.2×SSC, 0.1% SDS for 45 minutes each. Positive plaques were isolated and rescreened. A total of 18 positive plaques were identified.

The cDNA inserts from the positive plaques were amplified by PCR and subcloned. Briefly, agar plugs containing positive phage plaques were picked, and resuspended in 10 mM Tris, 1 mM EDTA to elute phage. A PCR reaction was set up with phage eluate and primers specific for the region of lambda gt11 flanking the insert. The individual amplification products were digested with EcoRI, purified by gel electrophoresis and QIAEX II™ gel extraction kit (Qiagen), and inserted into pUC9 at the EcoRI site. The subcloned inserts ranged in size from 1.0–3.3 kb.

Nine of the plasmids were purified using a QIAGEN™ plasmid kit according to the manufacturer's instructions, and sequenced automatically (Prism, Applied Biosystems, Foster City, Calif.). The sequences were assembled, edited and analyzed using a suite of programs, including the BLASTN program (described in Altshul et al. (1990) *J. Mol. Bio.* 215:403–410), and for overlaps using the AssemblyLIGN program (Kodak, N.Y.). The human Form I cDNA sequence is shown in SEQ ID NO:6. The predicted amino acid sequence is shown in SEQ ID NO:7

Table of Sequences

| Sequence | Molecule | SEQ ID NO | Sequence | Molecule | SEQ ID NO |
|---|---|---|---|---|---|
| Mouse Form I cDNA | dsDNA | 1 | D7Pjn24 2.61F | primer primer | 13 14 |
| translation of above | amino acid | 2 | C13R C13F2 | primer primer | 15 16 |
| Mouse Form II cDNA | dsDNA | 3 | C13F3 C13R3 | primer primer | 17 18 |
| translation of above | amino acid | 4 | 2.40F 2.40R | primer primer | 19 20 |
| tub mutation | dsDNA | 5 | GAPDH | primer | 21 |
| Human Form I cDNA | dsDNA | 6 | GAPDH ET_3636.p01.a04 | primer probe | 22 23 |
| translation of above | amino acid | 7 | | | |
| D7Pjn11 | primer | 8 | ET_3636.p01.d01 | probe | 24 |
| D7Pjn11 | primer | 9 | tub | amino acid | 25 |
| D7Pjn12 | primer | 10 | translation | | |
| D7Pjn12 | primer | 11 | | | |
| D7Pjn24 | primer | 12 | | | |

It is evident from the above results that a novel gene associated with mammalian obesity has been identified and characterized in mice and humans. A splicing defect in the gene leads to retinal and cochlear degeneration, as well as maturity onset-obesity. These genes and gene products find use in diagnosis, therapy, and drug identification.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule comprising a continuous open reading frame that encodes a tubby polypeptide consisting of the amino acid sequence as set forth in SEQ ID NO:2, or SEQ ID NO:7.

2. The isolated nucleic acid molecule according to claim 1, wherein said isolated nucleic acid molecule comprises a transcriptional initiation region 5' to said nucleotide sequence that encodes a tubby polypeptide.

3. An isolated nucleic acid molecule comprising the nucleotide sequence of SEQ ID NO:6 and that encodes a human tubby polypeptide consisting of the amino acid sequence as set forth in SEQ ID NO:7.

4. An isolated cell transfected with a nucleic acid molecule comprising a continuous open reading frame that encodes a human tubby polypeptide consisting of the amino acid sequence as set forth in SEQ ID NO:7.

5. An isolated nucleic acid molecule comprising the nucleotide sequence of SEQ ID NO:1 and that encodes the mouse tubby polypeptide consisting of the amino acid sequence as set forth in SEQ ID NO:2.

6. An isolated cell transfected with a nucleic acid molecule comprising a continuous open reading frame that encodes a mouse tubby polypeptide consisting of the amino acid sequence as set forth in SEQ ID NO:2.

* * * * *